(12) United States Patent
Harris

(10) Patent No.: US 9,693,611 B2
(45) Date of Patent: Jul. 4, 2017

(54) SAFETY BATON

(71) Applicant: Melvin Harris, Maywood, CA (US)

(72) Inventor: Melvin Harris, Maywood, CA (US)

( * ) Notice: Subject to any disclaimer, the term of this patent is extended or adjusted under 35 U.S.C. 154(b) by 26 days.

(21) Appl. No.: 14/794,711

(22) Filed: Jul. 8, 2015

(65) Prior Publication Data
US 2017/0009980 A1 Jan. 12, 2017

(51) Int. Cl.
*A45B 3/02* (2006.01)
*F21V 33/00* (2006.01)
*F21V 23/04* (2006.01)
*H02J 7/00* (2006.01)

(52) U.S. Cl.
CPC ............... *A45B 3/02* (2013.01); *F21V 23/04* (2013.01); *F21V 33/0076* (2013.01); *H02J 7/0042* (2013.01); *A61H 2201/0188* (2013.01)

(58) Field of Classification Search
CPC .... A45B 3/00; A45B 3/02; A61H 3/00; A61H 2201/5058; F21V 23/04; H02J 7/0042
USPC ..... 135/65–66, 910; 280/819, 821; 362/102, 362/208
See application file for complete search history.

(56) References Cited

U.S. PATENT DOCUMENTS

| 4,600,974 | A |  | 7/1986 | Lew et al. |
| 4,625,742 | A | * | 12/1986 | Phillips ............. A45B 3/04 135/66 |
| 4,957,057 | A |  | 9/1990 | Marcucci |
| 4,986,295 | A | * | 1/1991 | Kellner ................ A45B 3/00 135/66 |
| 5,003,437 | A | * | 3/1991 | Barrett ................. F21L 11/00 114/221 R |
| 5,086,377 | A |  | 2/1992 | Roberts |
| 5,197,501 | A | * | 3/1993 | Ragatz ................. A45B 3/00 135/66 |
| 5,577,827 | A | * | 11/1996 | Leffingwell .......... A45B 3/00 135/66 |
| 5,839,461 | A |  | 11/1998 | Lambeth |
| 5,973,618 | A |  | 10/1999 | Ellis |
| 6,745,786 | B1 | * | 6/2004 | Davis .................. A45B 3/00 135/65 |
| 6,933,855 | B2 | * | 8/2005 | Preston ................ G08B 7/06 135/66 |
| 7,267,281 | B2 | * | 9/2007 | Hopkins ............... A61H 3/061 135/911 |
| 7,654,275 | B2 |  | 2/2010 | Ewell et al. |

(Continued)

*Primary Examiner* — Winnie Yip
(74) *Attorney, Agent, or Firm* — The Keys Law Firm PLLC

(57) ABSTRACT

An electronic safety baton for providing a portable, multi-function security apparatus which includes both visual and audible interface is embodied as a baton housing that externally includes a lighting element, a speaker, a display screen, pulse sensors, two manual actuators, and a baton charging surface, internally includes a rechargeable battery, and utilizes a discrete floor charger mat. The electrically interconnected components on and in the baton housing enable a pulse reading system, a lighting system, and a panic system, each of which use electricity from the battery and are activated through manual engagement. The baton charging surface, when engaged with the floor charger mat, enables the recharging of the battery by allowing externally sourced electricity to be directed to the battery.

3 Claims, 1 Drawing Sheet

(56) References Cited

U.S. PATENT DOCUMENTS

| | | | | |
|---|---|---|---|---|
| 8,627,839 B1* | 1/2014 | Martinez | ............... | A45B 3/00 135/66 |
| 9,044,374 B1* | 6/2015 | Stimpson | ............... | A61H 3/061 |
| 2005/0011882 A1* | 1/2005 | Kim | ............... | H05B 1/0277 219/528 |
| 2008/0072940 A1* | 3/2008 | Cheng | ............... | A45B 3/00 135/66 |
| 2009/0038663 A1 | 2/2009 | Juslin et al. | | |
| 2009/0199884 A1 | 8/2009 | Lessing | | |
| 2009/0223546 A1 | 9/2009 | Nazarian | | |
| 2013/0346021 A1* | 12/2013 | Stevens | ............... | A45B 3/00 702/160 |

\* cited by examiner

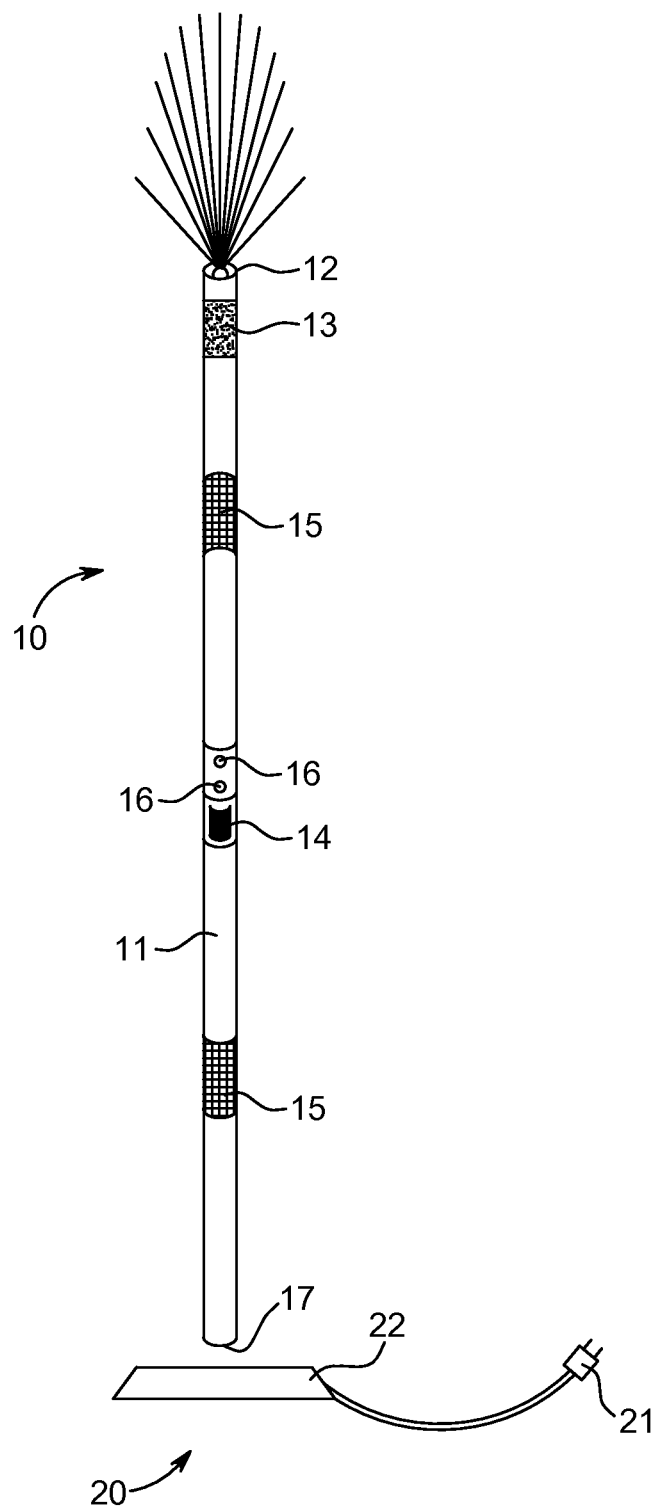

SAFETY BATON

BACKGROUND OF THE INVENTION

Field of the Invention

This invention relates generally to safety devices and, more particularly, to a portable safety baton for use while walking or jogging that includes an integrated flashlight, panic button and pulse reader.

Description of the Prior Art

The use of personal safety devices, such as sticks, sprays, and alarms, for protection while traversing outdoor environments is well known. A problem which still exists, however, is that most typical conventional safety devices are not designed with a plurality of discretely operated safety components that include both structural and electronic aspects which promote safety and/or protect a user. Thus, there remains a need for an electronic safety baton which combines various electronic aspects into a rigid, elongated cane structure suitable to be carried while walking or jogging. It would be helpful if such an electronic safety baton included discrete manual actuators, a visual display and speakers for providing plural user interfaces. It would be additionally desirable for such an electronic safety baton to include a rechargeable internal power source for supplying electrical power to the electronic components while being carried around.

The Applicant's invention described herein provides for an electronic safety baton adapted to be carried around outdoors to avail to a user a plurality of discrete safety features while traversing outdoor environments. The primary components in Applicant's electronic safety baton apparatus are a baton housing, a pulse reading system, a lighting system, and a panic system. When in operation, the electronic safety baton avails to a walking or jogging user a plurality of electronic and structural safety features from a single carried item. As a result, many of the limitations imposed by prior art structures are removed.

SUMMARY OF THE INVENTION

An electronic safety baton for providing a portable, multifunction security apparatus which includes both visual and audible interface functionality, as well as heart rate measurement functionality. The electronic safety baton is embodied as a baton housing that externally includes a lighting element, a speaker, a display screen, pulse sensors, two manual actuators, and a baton charging surface, internally includes a rechargeable battery, and utilizes a discrete floor charger mat. The electrically interconnected components on and in the baton housing enable a pulse reading system, a lighting system, and a panic system, each of which use electricity from the battery and are activated through manual engagement. The baton charging surface, when engaged with the floor charger mat, enables the recharging of the battery by allowing externally sourced electricity to be directed to the battery.

It is an object of this invention to provide an electronic safety baton which combines various electronic aspects into a rigid, elongated cane structure suitable to be carried while walking or jogging.

It is another object of this invention to provide an electronic safety baton that includes discrete manual actuators, a visual display and speakers for providing plural user interfaces.

It is yet another object of this invention to provide an electronic safety baton that includes a rechargeable internal power source for supplying electrical power to the electronic components while being carried around.

These and other objects will be apparent to one of skill in the art.

BRIEF DESCRIPTION OF THE DRAWINGS

FIG. 1 is an elevational view of an electronic safety baton built in accordance with the present invention.

DETAILED DESCRIPTION OF THE INVENTION

Referring now to the drawings and in particular the FIG. 1, an electronic safety baton 10 is shown as a baton housing 11 and a floor charger mat 20. The baton housing 11 defines a rigid, elongated housing which, in the preferred embodiment, measures between three (3) feet and five (5) feet. Externally, the baton housing includes a lighting element 12, a speaker 13, a display screen 14, two pulse sensors 15, two manual actuators 16, and a baton charging surface 17. The floor charger mat 20 defines a electrical power charger that includes an electrical plug 21 electrically connected to a charger transfer surface 22 so as to allow electricity available from a conventional electrical wall outlet (not shown) to be delivered to a conductive structure in contact with the charger transfer surface 22.

The lighting element 12 is disposed at one end of the baton housing 11 and defines a high beam light operative to selectively provide bright, long-range illumination. At the end of the baton housing 11 opposing the lighting element 12 is the baton charging surface 17. The baton charging surface 17 defines a flat, conductive surface which, when placed in contact with the charger transfer surface 22, is operative receive electrical power therefrom.

The lighting element 12, speaker 13, display screen 14, pulse sensors 15, manual actuators 16, and baton charging surface 17 are all electrically interconnected with each other and an internal battery inside the baton housing 11, thereby enabling a pulse reading system, a lighting system, and a panic system that operate using electricity in the battery. It is contemplated that electricity received by the baton charging surface 17 is directed to and stored in the battery.

The pulse reading system includes the pulse sensors 15 and the display screen 14, with the pulse sensors 15 operative as conventional pulse sensors to find one's pulse through the skin of their hands and generate a pulse electrical signal representing an estimate of the number of times one's heart is beating per minute in response to one holding their hands against them. Whenever a pulse electrical signal is generated by the pulse sensors 15, it is transmitted to the display screen 14 which then displays in Arabic numbers the number which corresponds to the beats per minute measurement. Accordingly, the pulse reading system is activated by a user holding their hands over both pulse sensors 15 simultaneously.

The lighting system includes the lighting element 12 and a dedicated one of the manual actuators 16. The manual actuator 16 dedicated to the lighting system defines a spring loaded button connected to an internal electrical switch, defined in one embodiment as a momentary switch, which controls the selective provision of electricity from the battery to the lighting element 12, thereby providing manual control of the illumination of the lighting element 12 through the manual actuator 16 dedicated to the lighting system.

The panic system includes the speaker 13 and a dedicated one of the manual actuators 16. As there are two manual actuators 16, it is contemplated that one will be dedicated to the lighting system and the other will be dedicated to the panic system. The manual actuator 16 dedicated to the panic system also defines a spring loaded button connected to an internal electrical switch, defined in one embodiment as a momentary switch, which controls the selective provision of electricity from the battery to the speaker 13. Upon being supplied with electricity, the speaker 13 broadcasts an audible alert sound. Accordingly, manual control of the broadcast of the audible alert sound of the panic system is provided through the manual actuator 16 dedicated to the panic system.

In one embodiment, the electrical switch dedicated to the panic system requires that the manual actuator 16 dedicated to the panic system be actuated for a predetermined period of time before the switch is activated to provide electricity to the speaker 13. It is contemplated that the period of time may define five (5) seconds so as to avoid accidentally activating the panic system.

In one embodiment, the display screen 14 defines a LED screen.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An electronic safety baton, comprising:
   a baton housing defining a rigid, elongated housing having a proximal end and a distal end and which includes a lighting element, a speaker, a display screen, at least one pulse sensor, at least one manual actuator, and a baton charging member which are each electrically interconnected with an internal battery, wherein the baton charging member defines a conductive baton charging surface disposed on the distal end;
   a charging device configured operatively engage with the baton charging member and direct electricity from a conventional power grid to the internal battery by way of the baton charging member, wherein the charging device defines a floor charger mat that includes an electrical plug electrically connected to a conductive charger transfer surface;
   said at least one manual actuator and said lighting element together being operatively connected to a lighting electrical switch disposed in the baton housing such that manual actuation of the at least one manual actuator enables selective provision of electricity from the internal battery through the lighting electrical switch, wherein the provision of electricity to said lighting element causes it to illuminate;
   said at least one manual actuator and said speaker together being operatively connected to a speaker electrical switch disposed in the baton housing such that manual actuation of the at least one manual actuator enables selective provision of electricity from the internal battery through the speaker electrical switch, wherein the provision of electricity to said speaker causes it to broadcast of the audible alert sound; and
   said at least one pulse sensor and said display screen being operatively connected such that when the at least one pulse sensor senses small electrical signals passing through skin, a pulse electrical signal is and transmitted to the display screen, wherein the transmission of a pulse electrical signal to said display screen causes the display screen to display a beats per minute measurement.

2. The electronic safety baton of claim 1, wherein the lighting element is disposed on the proximal end.

3. The electronic safety baton of claim 1, wherein the baton housing includes a discrete lighting manual actuator and a discrete panic manual actuator, with the lighting manual actuator configured to solely control the provision of electricity from the internal battery through the lighting electrical switch and the panic manual actuator configured to solely control the provision of electricity from the internal battery through the speaker electrical switch.

* * * * *